United States Patent
Björklund et al.

(10) Patent No.: US 6,524,291 B1
(45) Date of Patent: Feb. 25, 2003

(54) ABSORBENT ARTICLE SUCH AS A SANITARY NAPKIN, AN INCONTINENCE GUARD, A PANTY-LINER OR THE LIKE

(75) Inventors: Camilla Björklund, Mölnlycke (SE); Urban Widlund, Pixbo (SE); Ann Samuelsson, Lindome (SE); Solgun Drevik, Mölnlycke (SE); Anders Gustafsson, Billdal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/297,637
(22) PCT Filed: Nov. 11, 1997
(86) PCT No.: PCT/SE97/01885
§ 371 (c)(1), (2), (4) Date: Aug. 4, 1999
(87) PCT Pub. No.: WO98/22061
PCT Pub. Date: May 28, 1998

(30) Foreign Application Priority Data

Nov. 15, 1996 (SE) .............................. 9604224

(51) Int. Cl.$^7$ ................................................. A61F 13/15
(52) U.S. Cl. ........................ 604/385.03; 604/385.31; 604/387
(58) Field of Search .............. 604/385.01, 385.03, 604/385.21, 385.23, 386, 387, 385.31

(56) References Cited

U.S. PATENT DOCUMENTS

| 810,119 A | 1/1906 | Green |
|---|---|---|
| 810,120 A | 1/1906 | Green |
| 810,131 A | 1/1906 | Green |
| 1,946,626 A | 2/1934 | Jurgensen |
| 2,551,663 A | 5/1951 | Fox |
| 3,407,814 A | 10/1968 | George et al. |
| 3,468,311 A | 9/1969 | Gallagher |

(List continued on next page.)

FOREIGN PATENT DOCUMENTS

| EP | 0 067 377 A2 | 12/1982 |
|---|---|---|
| EP | 155 515 A1 | 9/1985 |
| EP | 0 235 763 A1 | 9/1987 |

(List continued on next page.)

OTHER PUBLICATIONS

U.S. application Ser. No. 09/297,366, filed Jul. 7, 1999; Inventors: Anette Johansson et al. (WO 98/22060).

(List continued on next page.)

*Primary Examiner*—Dennis Ruhl
*Assistant Examiner*—Jamisue Webb
(74) *Attorney, Agent, or Firm*—Burns, Doane, Swecker & Mathis, LLP

(57) ABSTRACT

The invention relates to an absorbent article such as a sanitary napkin, an incontinence guard, or a panty-liner, which article has a substantially elongated shape with a longitudinal direction and a transverse direction and also exhibits two side edges (9, 10), a front edge (11) and a rear edge (12), a front portion (6) and a rear portion (7), and a crotch portion (8) situated between the front portion (6) and the rear portion (7), which article furthermore exhibits a liquid-impervious surface (2) and a liquid-impervious surface (3). At least within the front portion (6) and the crotch portion (8), the article exhibits high bending stiffness against bending along transversely extending bending lines, whereby the front portion (6) and the crotch portion (8) of the article exhibit high shape permanence during use of the article. Furthermore, the front portion (6) of the article is angled in relation to the crotch portion (8), in a direction towards the liquid-pervious surface (2), whereby the front portion (6) forms and angle α towards the crotch portion (8) which is substantially permanent during use.

16 Claims, 3 Drawing Sheets

U.S. PATENT DOCUMENTS

| | | | |
|---|---|---|---|
| 3,570,493 A | | 3/1971 | Olsson |
| 3,888,255 A | | 6/1975 | Shah et al. |
| 4,041,950 A | | 8/1977 | Jones, Jr. |
| 4,047,531 A | | 9/1977 | Karami |
| 4,195,634 A | | 4/1980 | DiSalvo et al. |
| 4,217,901 A | | 8/1980 | Bradstreet et al. |
| 4,351,340 A | | 9/1982 | McLeod |
| 4,386,932 A | | 6/1983 | Pitts |
| 4,536,181 A | | 8/1985 | Cook |
| 4,643,726 A | | 2/1987 | Gegelys |
| 4,673,403 A | | 6/1987 | Lassen et al. |
| 4,804,380 A | | 2/1989 | Lassen et al. |
| 4,828,555 A | | 5/1989 | Hermansson |
| 4,846,824 A | | 7/1989 | Lassen et al. |
| 4,865,597 A | | 9/1989 | Mason, Jr. et al. |
| 4,886,513 A | * | 12/1989 | Mason, Jr. et al. ...... 604/385.1 |
| 4,897,084 A | | 1/1990 | Ternström et al. |
| 4,911,701 A | | 3/1990 | Mavinkurve |
| 5,007,906 A | * | 4/1991 | Osborn, III et al. ..... 604/385.1 |
| 5,032,121 A | * | 7/1991 | Mokry .................... 604/385.2 |
| 5,074,855 A | | 12/1991 | Rosenbluth et al. |
| 5,074,856 A | * | 12/1991 | Coe et al. ................ 604/385.1 |
| 5,080,658 A | | 1/1992 | Igaue et al. |
| 5,098,422 A | | 3/1992 | Davis et al. |
| 5,114,419 A | | 5/1992 | Daniel et al. |
| 5,129,893 A | | 7/1992 | Thorén |
| 5,171,302 A | | 12/1992 | Buell |
| 5,181,563 A | | 1/1993 | Amaral |
| 5,197,959 A | * | 3/1993 | Buell ...................... 604/385.1 |
| 5,295,987 A | | 3/1994 | Widlund et al. |
| 5,354,400 A | | 10/1994 | Lavash et al. |
| 5,374,260 A | | 12/1994 | Lemay et al. |
| 5,383,868 A | | 1/1995 | Hyun |
| 5,454,802 A | | 10/1995 | Lindquist et al. |
| 5,460,623 A | | 10/1995 | Emenaker et al. |
| 5,545,156 A | | 8/1996 | DiPalma et al. |
| 5,558,656 A | | 9/1996 | Bergman |
| 5,569,231 A | | 10/1996 | Emenaker et al. |
| 5,591,150 A | | 1/1997 | Olsen et al. |
| H1634 H | | 2/1997 | Oetjen et al. |
| 5,624,421 A | | 4/1997 | Dabi et al. |
| 5,688,259 A | | 11/1997 | Osborn, III et al. |
| 5,695,324 A | | 12/1997 | Weirich |
| 5,704,931 A | | 1/1998 | Holtman et al. |
| 5,713,885 A | * | 2/1998 | Jorgenson et al. ....... 604/385.2 |
| 5,722,967 A | | 3/1998 | Coles |
| 5,741,241 A | | 4/1998 | Guidotti et al. |
| 5,827,258 A | | 10/1998 | McFall et al. |
| 5,849,003 A | | 12/1998 | Olsen et al. |
| 5,873,869 A | | 2/1999 | Hammons et al. |
| 5,919,178 A | | 7/1999 | Widlund |
| 5,957,909 A | | 9/1999 | Hammons et al. |
| 5,961,508 A | | 10/1999 | Mayer et al. |
| 6,020,536 A | | 2/2000 | Osterdahl et al. |
| 6,033,391 A | | 3/2000 | Osborne, III et al. |
| 6,042,575 A | | 3/2000 | Osborn, III et al. |
| 6,080,909 A | | 6/2000 | Osterdahl et al. |

FOREIGN PATENT DOCUMENTS

| | | | | |
|---|---|---|---|---|
| EP | 0 335 252 A2 | 10/1989 | | |
| EP | 0 335 253 B1 | 10/1989 | | |
| EP | 0 335 253 A1 | 10/1989 | | |
| EP | 0 336 578 A1 | 10/1989 | | |
| EP | 155 515 B1 | 12/1989 | | |
| EP | 0 339 041 B1 | 11/1991 | | |
| EP | 0 419 434 B2 | 5/1993 | | |
| EP | 0606082 A1 | * 7/1994 | ........... A61F/13/15 |
| EP | 606 082 A1 | 7/1994 | | |
| GB | 2 119 656 | 11/1983 | | |
| GB | 2 119 657 | 11/1983 | | |
| WO | 93/15702 | 8/1993 | | |
| WO | 93/21879 | 11/1993 | | |
| WO | 95/31165 | 11/1995 | | |
| WO | 96/26699 | 9/1996 | | |
| WO | 97/09015 | 3/1997 | | |
| WO | 98/22058 | 5/1998 | | |

OTHER PUBLICATIONS

U.S. application Ser. No. 09/297,365, filed Aug. 2, 1999; Inventors: Camilla Björklund et al. (WO 98/22057).

U.S. application Ser. No. 09/297,584, filed Aug. 12, 1999; Inventors: Camilla Björklund et al. (WO 98/22058).

U.S. application Ser. No. 09/297,583, filed Aug. 3, 1999; Inventors: Anders Gustafsson et al. (WO 98/22059).

U.S. application Ser. No. 09/297,746, filed Sep. 1, 1999; Inventors: Ann Samuelsson et al. (WO 98/22062).

* cited by examiner

ABSORBENT ARTICLE SUCH AS A SANITARY NAPKIN, AN INCONTINENCE GUARD, A PANTY-LINER OR THE LIKE

TECHNICAL FIELD

The invention relates to an absorbent article such as a sanitary napkin, an incontinence guard, or a panty-liner, which article has a substantially elongated shape with a longitudinal direction and a lateral direction and also exhibits two side edges, a front edge and a rear edge, a front portion and a rear portion, and also a crotch portion situated between the front portion and the rear portion, which article further exhibits a liquid-pervious surface layer and a liquid-impervious surface layer.

BACKGROUND

Conventional absorbent articles of the above-mentioned kind typically have a substantially flat shape. Since the lower abdomen of a woman typically does not exhibit a corresponding flat appearance, problems often arise both during application as well as during use of such articles. The contact of the article against the body becomes poorer and a gap easily forms between the article and the body of the user. This implies that there is a substantial risk of body exudate leaking out between the article and the body of the user.

In order to solve this problem, it has been proposed to bend the absorbent article in a longitudinal direction, so that it assumes the shape of an elongated liquid-collecting bowl. Such a shape conforms somewhat better to the body contour of the lower abdomen of a woman. Accordingly, in EP 155 515 it is disclosed how such an absorbent article is given a bowl-shaped appearance by means of the application of elastics in the longitudinal side edges of the article.

In WO 96/20679 an absorbent article is disclosed which comprises a resilient component and tensioning means in order to provide the article with a bowl-shaped appearance.

One problem with articles of the above-mentioned type is, however, that they do not conform to the anatomy of the user particularly well, but only exhibit a generally bowl-shaped appearance. In order to make them bendable by means of the elastic means, and in order not to cause discomfort to the user, the articles are manufactured from soft, flexible materials. This implies that they are easily deformed during use, which leads to even worse fit and possible leakage. It is, for instance, not unusual that the longitudinal side edges of the article are folded in over the liquid-receiving surface of the article, whereby the area accessible for absorption is considerably reduced. When sudden and heavy liquid flows occur, there is consequently a substantial risk that the liquid is not absorbed into the article, but instead flows onto the inwardly folded side edges and leaks out on the clothes of the user.

Another problem associated with an article of the above-mentioned type is that it does not fit well against the body and therefore does not stay in place in a natural way during use, but must be attached to the panties of the user by means of special attachment means such as glue-surfaces or the like. The contact of the article against the body therefore becomes largely dependent on the quality and the shape of the panties of the user. Since many women use their most worn-out panties during menstruation, the result will in many causes be poor contact against the body with entailing leakage of menstrual liquid.

Still another factor which affects the leakage security of such a known article is that the article, instead of being in contact with the body of the user when in use, tends to follow the movements of the panties when the user is moving. Due to this, the article may end up in an incorrect position in relation to the body. Apart from leading to an increased risk of leakage, the mobility of the article in relation to the body also implies that the user, in a very obvious way, is reminded of the presence of the article in the panties and thereby perceives the article as uncomfortable and indiscreet to wear.

PURPOSE OF THE INVENTION

One object of the present invention is to provide an absorbent article with high leakage security and good fit and user comfort. Still a further object of the invention is to provide an absorbent article which during use rests securely and comfortably in place in contact with the body of the user.

SUMMARY OF THE INVENTION

An article of the type discussed by way of introduction, in which the problems associated with such previously known articles have been essentially eliminated is, according to the invention, mainly characterized in that the article, at least within the front portion and the crotch portion, exhibits high bending stiffness against bending along bending lines extending in a transverse direction, whereby the front portion and the crotch portion of the article exhibit high shape permanence during use of the article, and also that the front portion of the article is inclined in relation to the crotch portion, in a direction towards the liquid-pervious surface, whereby the front portion forms an angle $\alpha$ with respect to the crotch portion which is substantially permanent during use.

Since the front portion of the article is angled upwards from the central portion so that the front portion of the article, in the longitudinal direction of the article, conforms in a better way to the shape of the mons veneris of the user, it is prevented that the article during use slides backwards on the user. During use, the angled front portion contacts the mons veneris of the user and functions as a stop plate which counteracts the article being fed backwards by the leg movements of the user. In order to obtain the desired braking function, it is necessary that the front portion and the crotch portion of the article are so stiff that the angle therebetween is essentially maintained even during use. For reasons of comfort, however, it may be convenient that the edge portions closest to the longitudinal sides of the article, and the front edge, respectively, are constituted by a less stiff material.

An article according to the invention is rigid to bending in a transverse direction, i.e. it resists bending along bending lines which extend in the transverse direction of the article. In this way, the article maintains the shape it has in the length direction during use. On the other hand, the article may allow for a certain degree of deformation by means of compression in the transverse direction. It may be an advantage if the article may adapt to some extent to the body movements of the user and to the gap between the legs of the user. Such deformation may be achieved in a controlled way if the material in the article is chosen in such a way that the edge portions of the article are soft and resilient, whereas a central, longitudinal portion of the article is stiff and incompressible. Another way of achieving controlled compression of the article is by means of providing it with longitudinal bending notches such as ridges, grooves, compressions, slits, or the like. It is an advantage if the compression of the article can take place with a certain elasticity, so that the article more or less resumes its original width when the compressive forces cease.

If, however, the article is designed so that its width at the narrowest point in the crotch portion does not exceed approx. 40 mm, and preferably does not exceed approx. 35 mm, it is possible to use articles which, when subjected to the forces which arise during use, are also completely rigid when bending along longitudinal bending lines.

Measurements have shown that all humans have a critical area in the groin portion between two muscle groups which extend from the inside of the base of the pelvis down along each thigh. The distance between the two muscle groups has thereby been found to be surprisingly similar for all individuals, independent of body shape and weight. Thus, the distance between the thighs of a user is of course affected by fatness, while the distance between the muscle groups in the crotch of the user is the same, independently of whether the user is thin, of normal weight or overweight. It has been shown that the fact which determines whether a user experiences discomfort in the form of pressure or chafing against the insides of the thighs is whether the absorbent article during use has a width which, in the critical area, considerably exceeds the distance between the muscle groups in the groin area. This distance has been found to be between approx. 30 mm and 35 mm, Furthermore, it has been shown that an article with a width which during use exceeds 40 mm in the critical area is perceived as uncomfortable by the majority of users. On the contrary, it is seldom perceived as unpleasant that an absorbent article presses against or displaces fatty tissue which may be present in the crotch area.

Where conventional deformable absorbent articles are concerned, the limited space in the crotch area of the user causes the articles to be compressed in an uncontrolled way between the legs of the user and to be creased in order to be accommodated between the groins. When an absorbent article according to the invention is concerned, having a very stiff shape element in the crotch portion, compression may only take place to a limited extent, whereby the degree of possible compression is controlled by the design of the stiff crotch portion. It is therefore essential that the width of the absorbent article in the crotch portion during use does not exceed the critical value which can be tolerated by the user.

It is, however, not necessary that the crotch portion has a width along its entire length which, during use, is less than 40 mm. Since the critical area in the crotch region of the user is approx. 5 mm to 15 mm long, it is sufficient if the part of the crotch portion, which during use is intended to be arranged within this area, fulfils the requirement of a maximum width. Accordingly, it is sufficient for the invention if, in the longitudinal direction of the article, there is a 5–15 mm long area in the crotch portion within which the width during use of the article is no larger than approx. 40 mm and preferably is no larger than approx. 35 mm.

The stiffness of an absorbent article is to a high degree dependent on the shape of the article, particularly the shape of those components which exhibit high stiffness. A stiffening member, having beams in the form of ridges or grooves, consequently has a higher stiffness perpendicularly to the extension direction of the ridges or grooves than a completely flat material. The beams may be achieved by means of forming the material itself, or by means of reinforcing it with strips or ribs of another material. Furthermore, the stiffness and the resistance towards bending and twisting may be increased by imparting a bowl-shape to the material, or by means of increased material thickness.

The desired stiffness may advantageously be achieved by means of providing the article with, for instance, a liquid-arresting cover layer on the side which is intended to face away from the user when the article is used, which cover layer, at least at the front and central portion of the article, may be constituted by a rigid plastic layer. Such a plastic layer may, for instance, be shaped by means of casting or vacuum forming into a stable shell, inside which an absorbent body is placed. Typically, the absorbent body is covered by a liquid-pervious cover layer on the side of the article which during use is intended to face the user. Depending on the structure of the absorbent body, it is however not always necessary to use a special liquid-pervious cover layer. Accordingly, for instance, an absorbent foam layer, or a layer of absorbent fibre fabric, so-called nonwoven material, may constitute a component of an absorbent body and at the same time serve as a liquid-pervious cover layer.

As an example of plastic materials which have been found to have sufficient bending stiffness and torsional rigidity in order to achieve the shape stability necessary for the invention, one can mention polyethylene or polypropylene having a layer thickness of at least 0,4 mm. The material stiffness of a plastic film which is suitable for use as a stiffening element in an article according to the invention should exceed 100 N, as measured in accordance with ASTM D 4032-82 "Circular Bend Procedure", which method is described in detail in EP 0 336 578. In this context, material stiffness refers to the stiffness of a flat material layer.

When designing an absorbent article according to the invention, it is important to pay attention to the lower limit of the bending stiffness, since an article having a too low bending stiffness collapses when, during use, it is subjected to forces directed backwards. The upper stiffness limit is, however, not critical. On condition that an article according to the invention is given a shape which closely conforms to the body shape of the user, it has surprisingly been discovered that even extremely stiff and hard materials can be tolerated. Accordingly, it is, for instance, possible to use a shape-retaining insert of steel, aluminium, wood, or the like with such high bending stiffness that it does not permit deformation unless it is intentionally subjected to violence. Plates as well as rods and different types of skeleton-like constructions may be used.

It is not possible to specify a definite minimum value for the bending stiffness of flat materials which are suitable for achieving the desired stiffness of the finished article. Since a number of factors, beside the stiffness of the material itself, are of importance for the final stiffness of the article, the choice of material e.g. has to be adapted to the design of the article and to the stiffness of other components in the article.

One way of increasing the stiffness of a plastic layer is, by means of casting, bending, vacuum forming or in another way, to provide the stiffening element in the form of an originally flat material layer with a profile having elongated grooves, or ridges. Such a stiffening element exhibits a bending stiffness against bending perpendicularly to the extension of the grooves and ridges which is considerably increased in comparison to an untreated stiffening element. It is, of course, also possible to achieve increased stiffness by attaching stiffening material strips, rods, or the like, to the stiffening element. Furthermore, the stiffness of the article during use is affected if the crotch portion of the article is compressed in the transverse direction in the vicinity of the transitional area between the crotch portion and the front portion. Such compression namely increases the beam effect in the stiffening element and counteracts bending of the front portion in relation to the crotch portion.

Still another way of increasing the bending stiffness of a material layer is by laminating it with one or several additional material layers.

According to one embodiment of the invention, the front portion of the article is not only inclined with respect to the central portion, but is also curved in the longitudinal direction. In this manner, a better adaptation to the curved outline of the mons veneris of the user is achieved. In a corresponding way, the front portion may be curved in the transverse direction of the article, whereby the front portion assumes a bowl-shaped appearance which gives the article a very good fit around the mons veneris. By bending the front portion of the article in the longitudinal direction and/or in the transverse direction, a number of advantages are achieved. Accordingly, the improved fit causes the article to stay more securely in place during use, whereby leakage-security is enhanced. Furthermore, the anatomically adapted shape results in the article, although being very stiff, not being perceived as being uncomfortable to wear and does not protrude even under tight clothes. A further advantage with a bowl-shaped front portion is that the stability of the article and the resistance to deformation are increased. In particular, the resistance to compression in the crotch portion of the article is increased.

An anatomically designed article, according to the invention, is kept securely and comfortably in position against the body of the user during use, without the need for particular attachment means. This implies that the article is completely detached from the panties of the user, whereby the risk that the article moves with the panties during use, and thereby ends up in an incorrect position in relation to the body of the user, is almost completely eliminated.

BRIEF DESCRIPTION OF THE DRAWINGS

In the following, the invention will be described in greater detail with reference to the embodiments which are shown in the attached drawings, whereby.

DETAILED DESCRIPTION OF PREFERRED EMBODIMENTS

Figure 1:
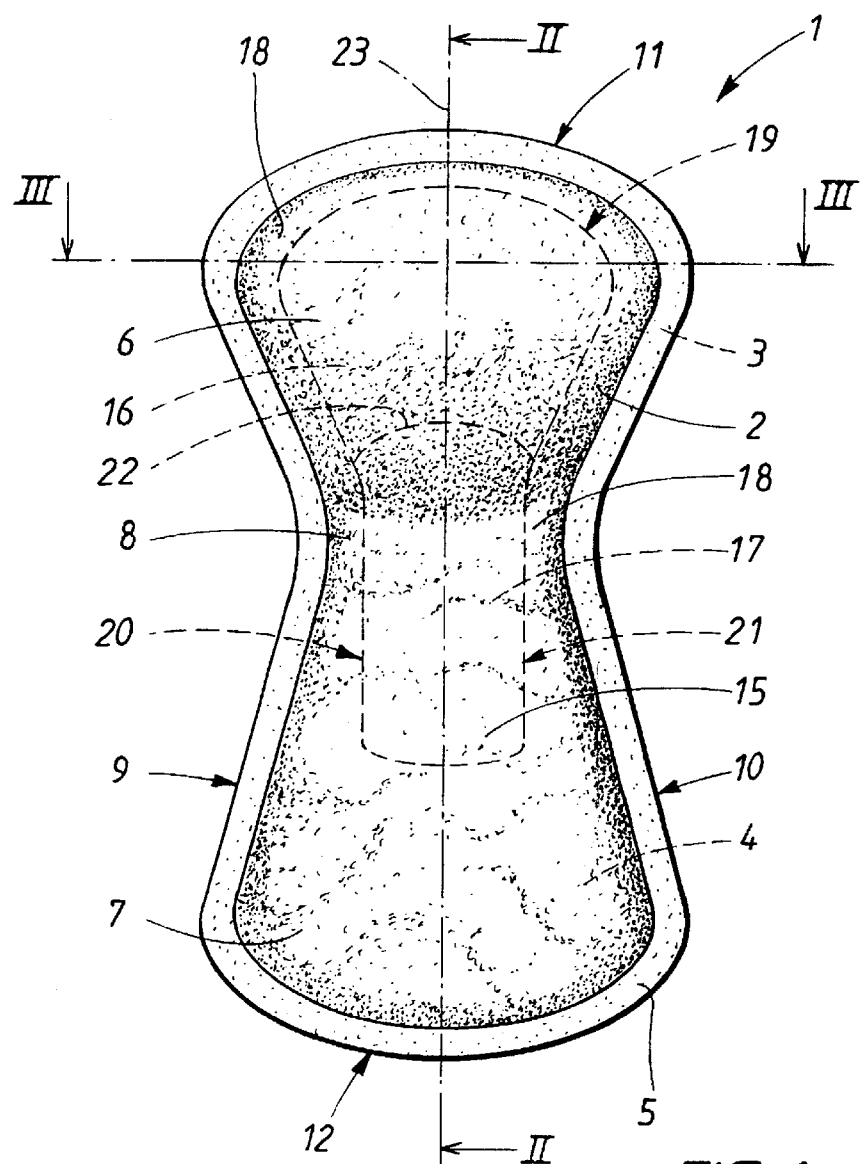
FIG. 1 shows a sanitary napkin according to the invention.
Figure 2:
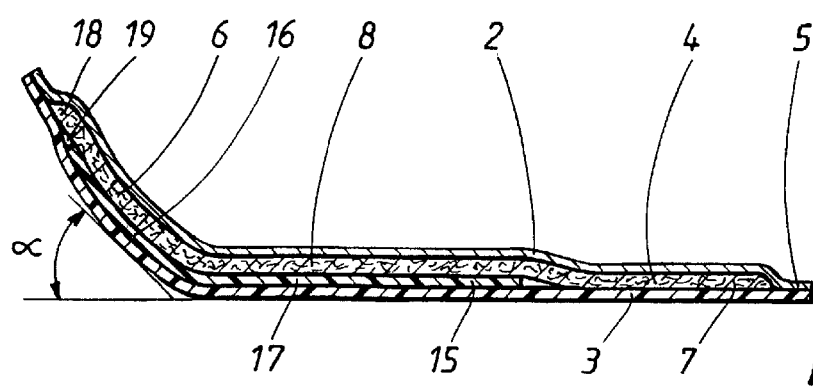
FIG. 2 shows a section along the line II—II through the sanitary napkin in FIG. 1.
Figure 3:
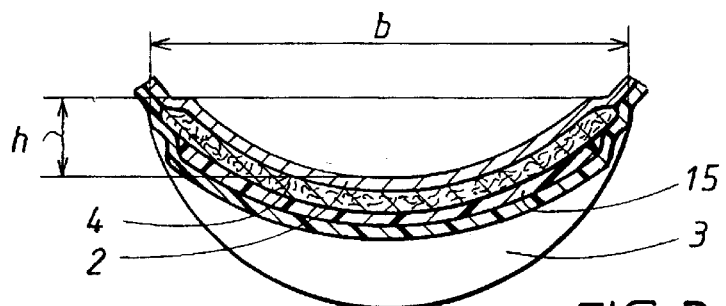
FIG. 3 shows a section along the line III—III through the sanitary napkin in FIG. 1.

The sanitary napkin 1 shown in FIGS. 1, 2 and 3 comprises a liquid-pervious cover layer 2 arranged on the side of the sanitary napkin 1 which, during use, is intended to face the user, a liquid-impervious cover layer 3 arranged on the side of the sanitary napkin 1 which, during use, is intended to be facing away from the user, and an absorbent body 4 enclosed between the two cover layers 2, 3.

The material of the liquid-pervious cover layer 2 may, for instance, be a perforated plastic film, a plastic scrim or a textile material, a nonwoven material or a laminate of, for instance, a perforated plastic film and a nonwoven sheet. The plastic material is typically thermoplastic, such as polyethylene or polypropylene. The expression "nonwoven material" refers to a non-woven fibrous web. Suitable nonwoven materials may consist of natural fibres, such as cellulose or cotton, or synthetic fibres such as polyethylene, polypropylene, polyester, polyurethane, nylon or regenerated cellulose. Naturally, it is also possible to use nonwoven materials made from fibre blends.

The liquid-pervious cover layer 2 is intended to receive and conduct the liquid into the absorbent body 4. Furthermore, the cover layer 2 should be soft and pleasant against the body of the user, as well as being able to prevent so-called rewetting, i.e. that absorbed body exudate forces its way back towards the skin of the user. For reasons of comfort, and in order to avoid skin irritation, it is important that the surface on the portion of the sanitary napkin which contacts the skin of the user be maintained as dry as possible during use. Furthermore, a dry surface on the sanitary napkin is perceived by the user as being cooler and more pleasant during use, and is both from a purely visual aspect, and when handling the sanitary napkin when this is to be changed, more attractive than a soiled, wet surface.

It is not necessary for all embodiments of the invention that the liquid-pervious cover layer 2 does in fact constitute a separate material layer. The liquid-pervious cover layer may, for instance, constitute an integral part of an absorbent body. Thus, it is conceivable that the liquid-pervious cover layer be omitted should the absorbent body comprise an absorbent foam layer. Furthermore, an absorbent nonwoven material may be utilized, which may be a component of an absorbent body and at the same time constitute a liquid-pervious cover layer.

The liquid-impervious cover layer 3 consists of a liquid-impermeable material. Thin, liquid-impervious plastic films are suitable for the purpose. It is, however, also possible to use materials which are originally liquid-pervious but which have been provided with a coating of plastic, resin, or other liquid-impervious material. In this manner, leakage of liquid from the bottom side of the absorbent article is prevented. The liquid-impervious cover layer 3 may accordingly consist of any material which is skin-friendly and which fulfils the criteria of liquid-impermeability. Examples of materials which are suitable as barrier layers are plastic films, nonwoven materials and different types of laminates. Useful plastic films are, for instance, those which consist of polyethylene, polypropylene, or polyester. Alternatively, the liquid-impervious cover layer 3 may consist of a laminate of a liquid-impermeable plastic layer facing the absorbent body and a nonwoven sheet facing the underclothing of the user. Such a construction provides a leakage-proof barrier layer with a textile feel.

As with the liquid-pervious cover layer 2, it is not necessary that the liquid-impervious cover layer 3 be constituted by a separate layer. Accordingly, it is conceivable that the liquid-impervious cover layer 3 constitutes an integral part of an absorbent material, for instance an absorbent foam layer with a liquid-impervious surface.

The absorbent body 4 may advantageously be primarily constituted by cellulose fluff pulp. The fluff may be present in the form of reels, bales or sheets which are dry shredded and transformed in a fluffed state into a pulp mat, with or without the admixture of so-called super-absorbents, which are polymers with an ability to absorb several times their own weight of water or body exudate. Examples of other useful materials are different types of natural fibres such as cotton fibres, peat, or the like. It is, of course, also possible to utilize absorbent synthetic fibres, or blends of natural fibres and synthetic fibres. The absorption material may furthermore include further components, such as liquid-distributing members or binders such as e.g. thermoplastic fibres which have been heat-treated in order to bind short fibres and particles into a coherent unit. It is also possible to utilize different types of absorbent foam materials in the absorbent body 4.

The two cover layers 2, 3 are mutually connected outside the absorbent body 4 and form a protruding edge 5 around the entire periphery of the sanitary napkin. The joining of the cover layers may take place in any suitable way, such as by means of gluing, sewing, or welding either with heat or ultrasonically.

The sanitary napkin 1 is substantially hourglass-shaped and thereby exhibits a front portion 6, intended to be directed forwards on the user during use, a rear portion 7, intended to be directed backwards on the user during use, and an intermediate, narrower crotch portion 8 intended to be applied in the groin area of the user. Furthermore, the sanitary napkin 1 has two concavely-curved side edges 9, 10, a convexly-curved front edge 11, and a similarly convexly-curved rear edge 12.

The segmentation of the sanitary napkin into a front portion 6, a rear portion 7, and a crotch portion 8, should not be understood as implying that there are be sharp limits between the different portions 6–8, but is primarily intended to facilitate the description of the sanitary napkin with reference to the differences which are present between the different portions 6–8 depending on how they are intended to be placed in relation to the body of a user. Thus, the transition between the different portions 6–8 does not take place at fixed transverse lines, but rather within transitional areas situated at a distance of approximately one third of the length of the sanitary napkin from the front edge 11 and the rear edge 12 of the sanitary napkin, respectively. In this manner, the crotch portion 8 constitutes the part of the sanitary napkin which, in use, is intended to receive and absorb the major part of the liquid which during use is emitted to the sanitary napkin.

A shape-retaining element 15, for instance made of a rigid plastic layer or a rigid metal plate, is arranged between the liquid-impervious cover layer 3 of the sanitary napkin 1 and the absorbent body 4, and extends across the front portion 6 and the crotch portion 8 of the sanitary napkin.

The shape-retaining element 15 is shaped as a spoon, or scoop, with a cupped part 16 situated at the front portion 6 of the sanitary napkin and a rectangular flat part 17 situated at the crotch portion 8. The cupped part 16 of the shape-retaining element 15 has substantially the same planar shape as the front portion 6 of the sanitary napkin, but is slightly smaller. Thus, the parts of the front portion 6 which project past the edge 19 of the shape-retaining element 15 form a soft, cushioning edge area 18 which serves both as a leakage barrier as well as counteracting chafing. In a corresponding way, the flat part 17 of the shape-retaining element 15 does not extend all the way out to the side edges 9, 10 of the sanitary napkin in the crotch portion 8, but a narrow, soft and resilient edge area 18, consisting of portions of the two cover layers 2, 3 and the absorbent body 4, extends between each respective side edge and the corresponding side edges 20, 21 of the shape-retaining element 15.

The cupped part 16 of the shape-retaining element 15 is inclined in the longitudinal direction of the sanitary napkin with respect to the flat part 17, whereby the front portion 6 of the sanitary napkin 1 is also inclined with respect to the crotch portion 8, as is best observed in FIG. 2. In order to obtain-the desired inclination of the sanitary napkin, the shape-retaining element 15 is permanently curved or bent along a transverse folding line 22, which line is slightly curved in a direction towards the front edge of the sanitary napkin. The angle α between the substantially flat crotch portion 8 of the sanitary napkin and the front portion 6 raised therefrom is thereby approximately 20°–50° and preferably approximately 30°. In FIG. 2, the angle α is indicated on the outside of the sanitary napkin, i.e. the side of the sanitary napkin which in use is intended to be facing away from the user. The relevant angle is, however, in fact the angle on the inside of the sanitary napkin, since it is the inside which should conform to the anatomy of the user. In the shown example, it is of no significance whether the angle is measured at the outside or the inside, since the obtained value will be the same because both the front portion 6 and the crotch portion 8 have the same inclination on the inside and on the outside.

The curved folding line 22 contributes to providing the sanitary napkin with good shape stability by increasing the bending stiffness of the shape-retaining element 15 at the folding line 22. Thus, the angle between the cupped part 16 of the shape element 15 and its flat part 17 is maintained even when the sanitary napkin is subjected to forces during use. Furthermore, for fit and leakage security, the folding line provides the front portion 6 of the sanitary napkin with an advantageous cupped appearance, as shown in FIG. 3. At a width b of the front portion 6 which is between 80 and 100 mm, the curvature of the front portion 6 should not be larger than the maximum deviation h, from a straight transverse line between the side edges 9, 10 of the sanitary napkin, does not exceed approx. 10 mm in the vicinity of the front edge 11.

Consequently, the front portion 6 of the sanitary napkin is angled in a direction towards the liquid-pervious cover layer 2, which implies that the front portion 6 is raised in a direction towards the viewer, when the sanitary napkin is viewed with the liquid pervious cover layer 2 facing the viewer. Furthermore, the front portion 6 is advantageously curved along the longitudinal centre line 23 of the sanitary napkin in such a way that the front portion 6 is bowl-shaped as seen from the liquid-pervious cover layer 2. The bowl-shape should, however, not be more pronounced than that the longitudinal centre line deviates at the most 5 mm from a straight line extending along the centre line between the transverse folding line 22 and the front edge 11.

It is an essential aspect of the invention that the angle of the front portion of the sanitary napkin, in a direction upwards from the liquid-pervious cover layer 2, is permanent during use. In order to achieve this, the shape-retaining element 15 is made of a material with a stiffness which in this context must be regarded as being very high. For reasons of comfort, it is therefore necessary that the part of the shape-retaining element 15 which, during use, is intended to be applied in the groin area of the user, is not so wide that it causes discomfort to the user. As earlier mentioned, there is a critical area in the groin area within which the width of, for instance, a sanitary napkin cannot be allowed to exceed approx. 40 mm without discomfort to the user. For the sanitary napkin 1 shown in FIG. 1, this implies that the width of the flat portion 17 of the shape-retaining element 15 should not be larger than approx. 35 mm. Even if the width of the crotch portion 6 of the sanitary napkin in its entirety should exceed 35 mm, this is, however, not critical, since the soft edge areas 18 around the shape-retaining element 15 permit a certain degree of compression and adaptation of the width of the sanitary napkin 1 to the distance in the groin area of the user, whereby the width of the sanitary napkin after compression does not exceed approx. 40 mm.

Figure 4:
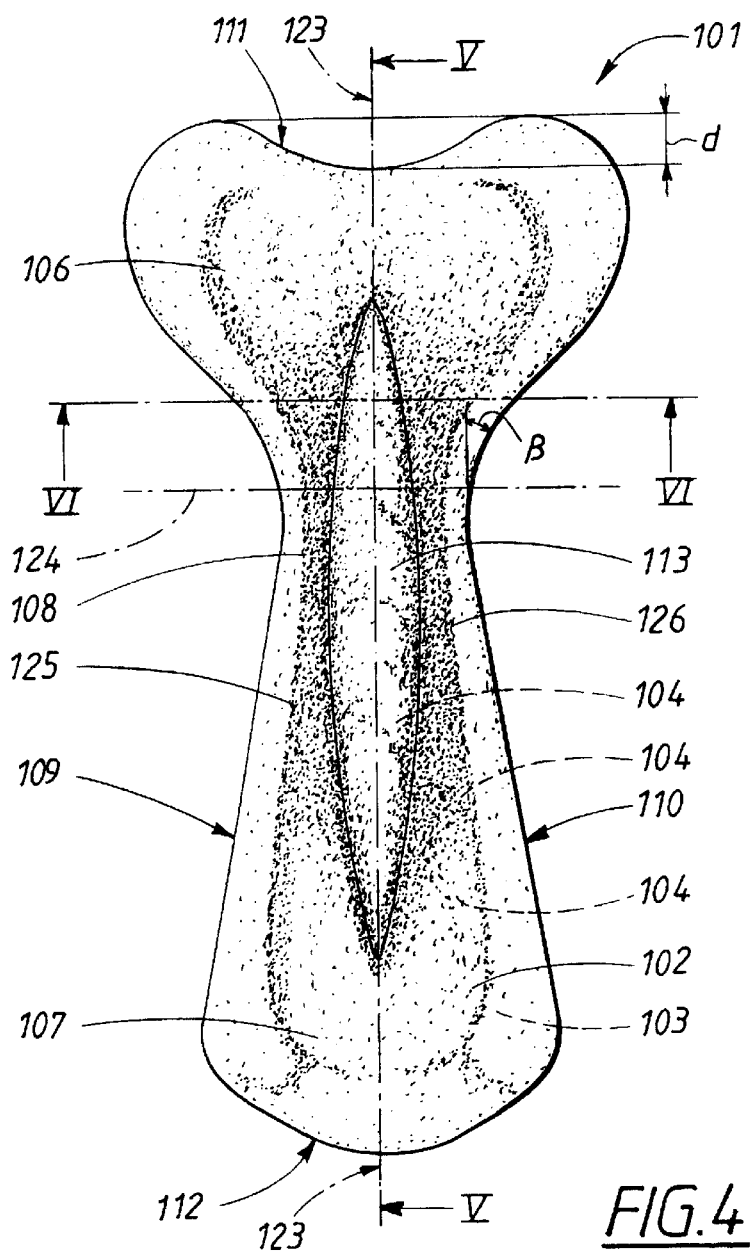
FIG. 4 shows a sanitary napkin according to an alternative embodiment of the invention.
Figure 5:
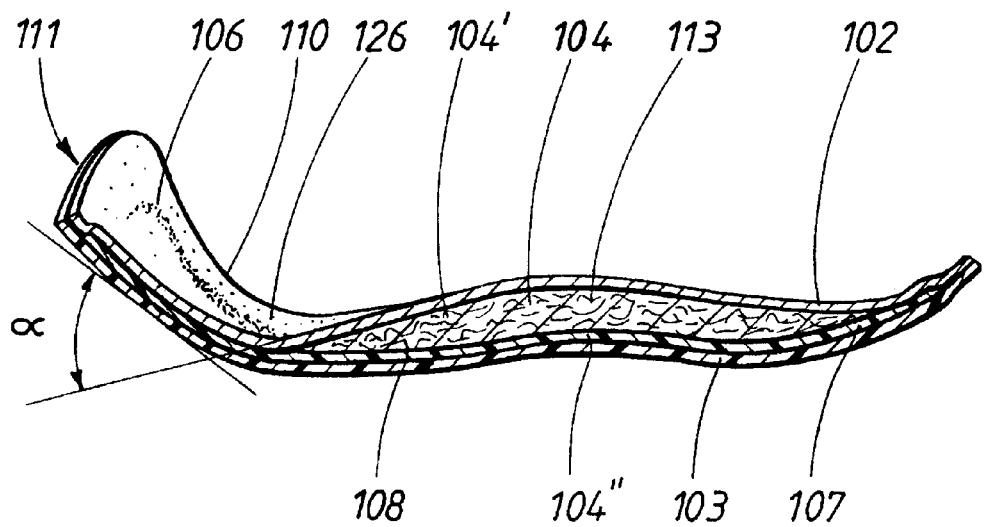
FIG. 5 shows a section along the line V—V through the sanitary napkin in FIG. 4
Figure 6:
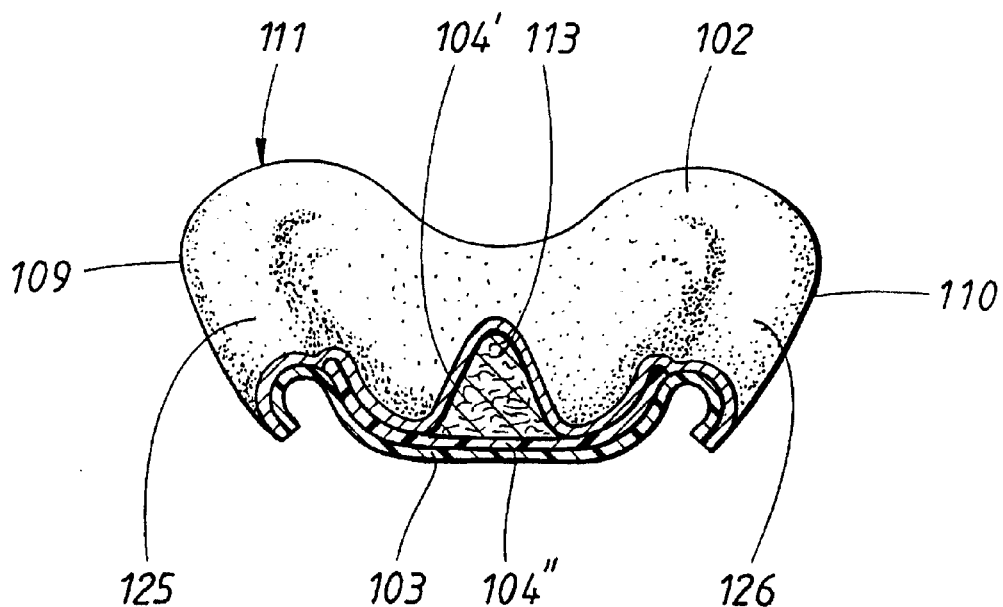
FIG. 6 shows a section along the line VI—VI through the sanitary napkin in FIG. 4.

The sanitary napkin 101 shown in FIGS. 4–6 comprises a liquid-pervious cover layer 102 as well as a liquid-impervious cover layer 103, which together enclose an absorbent body 104. The liquid pervious cover layer 102 is, as in the sanitary napkin 1 shown in FIGS. 1, 2 and 3, constituted by a soft, flexible, skin-friendly material. The liquid-impervious cover layer 103 is, however, constituted by a rigid material, preferably a comparatively thick, stiff plastic layer, which forms a hard, shape-retaining shell in which the absorbent body 104 is placed.

The sanitary napkin 101 is designed with a front portion 106 which is wider than the rear portion 107, and with a crotch portion 108 which is narrower than both the front portion and the rear portion. Since the liquid-impervious cover layer 103 is so stiff, it is namely essential that the napkin has a shape which to a very high degree is adapted to the anatomy of the user. Thus, it is of particularly great importance that the width of the sanitary napkin at least in the crotch portion 108 does not exceed approx. 40 mm.

Furthermore, the sanitary napkin 101 exhibits two longitudinal side edges 109, 110, a transverse concavely-curved front edge 111 and a transverse convexly-curved rear edge 112. The sanitary napkin is designed in such a way that, in the front portion of the crotch portion 108, there is a cross-sectional line 124, extending in the transversal direction of the sanitary napkin, which intersects the side edges 109, 110 of the sanitary napkin. At the cross-sectional line 124, the side edges 109, 110 change inclination in relation to the longitudinal centre line 123, whereby the width of the sanitary napkin increases in direction towards the front edge 111, whereby the front portion 106 exhibits a maximum width, which exceeds the width of the crotch portion 108 at the cross-sectional line 124. The maximum width of the front portion 106 is suitably at least twice the width of the crotch portion 108 at the cross-sectional line 124. The inclination of the side edges 109, 110 at the front portion 106 is defined by an angle β between each respective side edge 109, 110 and a longitudinal line parallel to the centre line 123, whereby β is between 30° and 90° and whereby the width of the crotch portion 108 at the cross-sectional line 124 is between 15 and 45 mm and preferably between 20 and 40 mm, If, however, the sanitary napkin has a construction similar to the one which is shown in FIG. 1, the width of the sanitary napkin may be allowed to be up to 60 mm.

The absorbent body 104 comprises a first portion 104', which forms a longitudinal hump 113 on the side of the sanitary napkin which in use is intended to face a user.

The first portion 104' consists of material with high absorption capacity, for instance absorbent fibres such as cellulose fluff pulp, rayon or the like, with or without super-absorbent material, absorbent foam or any of the above-described absorbent fibre materials. Furthermore, all conceivable types of blends and combinations of material layers may be used.

The absorbent body 104 of the sanitary napkin further comprises an absorption layer 104" arranged between the hump 113 and the liquid-impervious cover layer. The absorption layer 104" may comprise an absorbent nonwoven material, tissue paper or any one of the above-mentioned absorbent materials and may be designed with larger or smaller absorption capacity depending on the intended use of the sanitary napkin.

In the sanitary napkin shown in FIGS. 4–6, the shape of the napkin is maintained by means of the entire liquid-impervious cover layer 103 constituting a shape-retaining shell for the absorbent body 104 of the sanitary napkin. As in the sanitary napkin in FIGS. 1–3, the front portion 106 of the sanitary napkin 101 shown in FIGS. 4–6 is inclined in relation to the crotch portion 108 of the sanitary napkin. The angle α between the front portion 106 and the crotch portion 108 in FIG. 5 has been shown as being the angle between the inclination of the hump, along the longitudinal centre line 123 of the sanitary napkin, and the inclination of the front portion 106, since it is this inner angle which determines how well the sanitary napkin conforms to the shape of the body of the user in the relevant area. The upwards bending of the front portion 106, in relation to the crotch portion 108, does not occur along a sharp folding line, but instead the curvature is continuous in the longitudinal direction of the sanitary napkin. In this manner, the front portion 106 forms a softly rounded bowl which conforms very well to the anatomy of the user.

When determining the angle α, the curvature of the front portion 106 is disregarded so that the inclination of the front portion is determined in relation to a straight line which extends along the longitudinal centre line 123, from an imaginary transverse border line between the front portion 106 and the crotch portion 108, to the front edge 111. The exact value of the inclination of the front portion 106 in relation to the crotch portion is not vital, as long as the angle α is between 20° and 50°. It is, however, essential that the angle is permanent during use, both when the article is dry and when it has been wetted by body exudate.

In FIG. 6, there is shown a cross-section through the sanitary napkin 101, shown in FIGS. 4 and 5. As is clearly evident from FIG. 6, the side edges 109, 110 of the sanitary napkin are curved in a direction downwards-inwards, as seen from the liquid-pervious cover layer 102. This implies that the sanitary napkin exhibits rounded ridges 125, 126, along the side edges 109, 110, which edges during use of the sanitary napkin are intended to be in contact with the body of the user in the groin folds of the user. The rounded ridges 125, 126 extend along the side edges 109, 110, along practically the entire length of the sanitary napkin, but flatten out somewhat at the front edge 111 and the rear edge 112, respectively.

The raised ridges 125, 126 along the side edges 109, 110 of the sanitary napkin fulfil several functions. Firstly, they constitute reinforcement beams which increase the bending resistance when bending along substantially transverse bending lines. Secondly, the rounded surface which is directed towards the user contributes to increased user comfort. In addition, the ridges 125, 126 serve as means for controlling the compression of the crotch portion 108 of the sanitary napkin. In order to increase the bending stiffness also in the transversal direction of the sanitary napkin as well, it is of course possible to also arrange transverse reinforcement beams, for instance in the crotch portion 108.

In order to further increase the comfort for the user, the front portion 106 is provided with a recess at the front edge 111. The recess is formed by means of the front edge 111 being curved in a direction towards the crotch portion 108 of the sanitary napkin. Since the front edge 108 is concavely-curved, it conforms to the outline of the mons veneris of the user in a better way, for which reason the risk of chafing is almost non-existent.

The invention should not be regarded as being limited to the herein-described embodiments, instead a number of further variants and modifications are conceivable within the scope of the claims. For instance, the invention comprises all types of absorbent articles which are sized to be substantially accommodated in the groin area of a user. Furthermore, all conceivable combinations of the described embodiments are intended to be embraced by the invention.

What is claimed is:

1. An absorbent article having a substantially elongated shape with a longitudinal direction and a transverse direction, the absorbent article comprising:

two side edges, a front edge and a rear edge, said front edge defining a front portion, said rear edge defining a rear portion, a crotch portion situated between the front portion and the rear portion, a liquid-pervious cover layer and a liquid-impervious cover layer, wherein the front portion and the crotch portion of the absorbent article exhibit high shape permanence during use of the article, wherein the front portion of the absorbent article is inclined with respect to the crotch portion in a direction towards the liquid-pervious cover layer at a predetermined angle α of between 20° and 50°, the angle α being permanent while being worn irrespective of a wearer's leg movements.

2. The absorbent article according to claim 1, wherein the front portion is curved along a longitudinal centre line through the absorbent article.

3. The absorbent article according to claim 1, wherein the front edge of the absorbent article exhibits a recess by means of the front edge being curved in a direction towards the crotch portion of the absorbent article.

4. The absorbent article according to claim 1, wherein the absorbent article, at least within the front portion and the crotch portion, exhibits high bending stiffness against bending in the transverse direction along longitudinally extending bending lines.

5. The absorbent article according to claim 1, wherein the absorbent article is a sanitary napkin, an incontinence guard, or a panty liner.

6. The absorbent article according to claim 1, wherein the front portion is curved along a transverse line through the absorbent article, wherein the side edges of the absorbent article at the front portion are raised on both sides of the longitudinal centre line of the article so that the side edges are situated above the longitudinal centre line of the absorbent article when the absorbent article is viewed from the liquid-pervious cover layer.

7. The absorbent article according to claim 6, wherein a maximum deviation (h) from a transverse line between the side edges of the absorbent article does not exceed 10 mm at the front edge of the absorbent article.

8. The absorbent article according to claim 1, wherein longitudinal ridges having a rounded surface are arranged along the side edges of the absorbent article at least in the crotch portion.

9. The absorbent article according to claim 8, wherein the ridges are formed of a stiff sheet of material.

10. The absorbent article according to claim 1, wherein the crotch portion of the article exhibits a transversely extending cross-sectional line from which a width of the article increases in a direction toward at least one of the ends of the absorbent article, wherein the front portion has a maximum width which is larger than a width of the crotch portion at the cross-sectional line, wherein the long sides of the article change inclination at the transversely extending cross-sectional line, the inclination being defined by an angle β between a longitudinal line parallel to the direction of the article and each of the long sides of the absorbent article, respectively, wherein β is between 30° and 90°, and wherein the width of the crotch portion at the transversely extending cross-sectional line is at most 50 mm.

11. The absorbent article according to claim 10, wherein the width of the absorbent article at the cross sectional line is between 20 and 40 mm.

12. An absorbent article having a substantially elongated shape with a longitudinal direction and a transverse direction, the absorbent article comprising:

two side edges, a front edge and a rear edge, said front edge defining a front portion, said rear edge defining a rear portion, a crotch portion situated between the front portion and the rear portion, a liquid-pervious cover layer and a liquid-impervious cover layer, wherein the front portion and the crotch portion of the absorbent article exhibit high shape permanence during use of the article, wherein the front portion of the absorbent article is inclined with respect to the crotch portion in a direction towards the liquid-pervious cover layer at a predetermined angle α of between 20° and 50°, the angle α being permanent while being worn irrespective of a wearer's leg movements, and the absorbent article further comprising a rigid shape-retaining element, the rigid shape-retaining element comprising non-elastic material.

13. The absorbent article according to claim 12 wherein the rigid shape-retaining element comprises a stiff plastic sheet which also forms the liquid-impervious cover layer of the absorbent article.

14. The absorbent article according to claim 12, wherein the shape-retaining element extends across the front portion and the crotch portion of the absorbent article.

15. The absorbent article according to claim 12, wherein the rigid shape-retaining element extends across the front portion and the crotch portion of the absorbent article, is located between the liquid-pervious cover layer and the liquid-impervious cover layer, and exhibits a bending line extending in the transverse direction of the absorbent article, wherein a front part of the shape-retaining element is angled in relation to a back part of the shape-retaining element along the bending line of the shape-retaining element, and wherein an angle formed between the front part and the back part of the rigid shape-retaining element corresponds to the angle α between the front portion and the crotch portion of the absorbent article.

16. The absorbent article according to claim 15, wherein the bending line of the shape-retaining element is curved.

* * * * *